United States Patent [19]

Colebourne et al.

[11] 3,955,017

[45] May 4, 1976

[54] METHOD OF COATING METAL PHOSPHATES ON ORGANIC POLYMERIC SUBSTRATES

[75] Inventors: Neville Colebourne; Nicholas Rolfe; Kevin Thomas McAloon; Michael Leslie Orton, all of Runcorn, England

[73] Assignee: Imperial Chemical Industries Limited, London, England

[22] Filed: July 17, 1972

[21] Appl. No.: 272,498

[30] Foreign Application Priority Data

Nov. 26, 1971 United Kingdom............... 55001/71

[52] U.S. Cl................................ 427/383; 427/427; 427/428; 427/430; 428/418; 428/430; 428/450; 428/458; 428/462
[51] Int. Cl.²...................... B05D 3/04; B32B 15/08
[58] Field of Search............. 117/138.8 D, 138.8 E, 117/138.8 F, 138.8 R, 160 R, 139.5 CF, 169 R, 94, 95, 138, 151, 33.3; 252/8.6; 106/1, 15 FP, 286

[56] References Cited
UNITED STATES PATENTS

| | | | |
|---|---|---|---|
| 1,310,841 | 7/1919 | Robinson............................ | 117/138 |
| 1,434,549 | 11/1922 | Lewis et al.......................... | 117/138 |
| 2,563,637 | 8/1951 | Balthis et al........................ | 117/102 |
| 2,621,333 | 12/1952 | Thomas et al..................... | 117/169 R |
| 2,786,787 | 3/1957 | Florio................................. | 117/169 R |
| 3,042,542 | 7/1962 | Anders............................... | 117/33.3 |
| 3,248,251 | 4/1966 | Allen .................................. | 106/286 |
| 3,258,521 | 6/1966 | Francel et al....................... | 174/52 |
| 3,274,014 | 9/1966 | Harrington et al. ................ | 106/177 |
| 3,278,328 | 10/1966 | Okrent ........................ | 117/138.8 F |
| 3,298,861 | 1/1967 | Gagliardi .......................... | 117/138.8 |
| 3,309,218 | 4/1967 | Brader et al. ...................... | 117/33.3 |
| 3,650,807 | 3/1972 | Witschard............................ | 117/69 |
| 3,709,723 | 1/1973 | Watanabe et al.............. | 117/124 A |
| 3,821,014 | 6/1974 | Haskell et al................... | 117/46 FC |
| 3,853,591 | 12/1974 | Haskell et al..................... | 117/47 A |

*Primary Examiner*—P. E. Willis, Jr.
*Attorney, Agent, or Firm*—Cushman, Darby & Cushman

[57] ABSTRACT

An organic polymer article has a surface coating of a metal phosphate. The coating has a thickness in the range of 0.01 to 5 microns; preferably, the metal phosphate comprises a mixture of iron and titanium orthophosphate, although the metal may be chosen from the elements of a periodic table having an atomic number of 12, 14, 20 to 32, 39 to 50, 56 to 80, 90 or 92. A continuous coating of the metal phosphate is obtained by applying to the organic polymer article a solution of a compound of the metal wherein the solution contains an organic component. The solution is converted to the coating of the metal phosphate by drying.

9 Claims, No Drawings

METHOD OF COATING METAL PHOSPHATES ON ORGANIC POLYMERIC SUBSTRATES

This invention relates to coatings on organic polymers of chemical compositions of metals and complexes isolatable therefrom, particularly coatings of compositions and complexes containing organic ligands and ligands derived from oxyacids of phosphorus of arsenic. The compositions and complexes and their preparation are described in the co-pending U.S. patent application of Colebourne and Rolfe Ser. No. 272458, assignors to Imperial Chemical Industries Limited, which is based on U.K. Patent Applications 34012/71 and 58999/71.

Metals, for the purpose of the present specification, are defined as the elements of the periodic table of elements, having an atomic number of 12, 14, 20 to 32, 39 to 50, 56 to 80, 90 or 92. By an oxyacid of phosphorus or arsenic we mean a phosphorus or arsenic compound containing the group of structure (1)

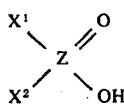
(1)

where Z is a phosphorus or arsenic atom, $X^1$ and $X^2$ are the same or different and selected from hydrogen, hydroxyl and halide, or, when Z is phosphorus, $X^2$ may have the structure (2) to provide pyrophosphate

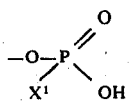
(2)

These oxyacids and ligands derived therefrom are referred to as phosphate and arsenate: within the term are included the meta-phosphate and arsenate and pyrophospate.

The invention has several aspects and these will be described under the following heading E. For convenience details of the compositions and complexes are also given under headings A to D.

A— The compositions
B — Complexes isolatable therefrom
C — Methods of preparing complexes
D — Properties of the complexes and their solutions
E — Uses of the compositions and complexes in forming coatings
F — Examples of products and processes under heading E A. The Compositions Our invention uses liquid metal-containing compositions which comprise a solution, in an at least partly organic, preferably oxygen-containing, solvent, of (a) a metal compound and (b) an oxyacid of phosphorus or arsenic or a compound capable of forming such an oxyacid in the solution. These compositions are capable of decomposing on heating to a metal phosphate or arsenate.

The organic solvent is preferably selected from alcohols, esters, ketones, aldehydes, nitro compounds and ethers, especially monohydric alcohols, ROH containing 1 to 10 carbon atoms, esters of the structure $R^1COOR^2$ where R, $R^1$ and $R^2$ are alkyl groups or substituted alkyl groups containing from 1 to 10 carbon atoms each, ethers of the structure $R^1OR^2$ and ketones of the structure $R^1COR^2$, where $R^1$ and $R^2$ have the meaning ascribed above, nitro compounds of the structure $R^1NO_2$ and ethers of the structure $OR^3$ where $R^3$ is a divalent alkyl group having from 4 to 7 carbon atoms one of which may be replaced by an oxygenation. Mixtures of one or more solvents may be used. Diluents may also be present, provided they do not bring about precipitation of the components of the composition. Up to 50% of aromatic or halogenated hydrocarbon diluents may be present. The effect of including larger amounts of such diluents will be discussed in detail later.

While phosphate and arsenate are used in this specification to cover oxyacids of phosphorus or arsenic in general, orthophosphate and orthoarsenate are preferred.

The metal-containing composition may be formed by dissolving a complex of the type described in Section B of this specification in a solvent. Alternatively a metal compound and an oxyacid of phosphorus or arsenic (or a source thereof, such as the acid anhydrides or an oxyhalide) are dissolved in a solvent for at least one component and the reaction product in the presence of organic ligands. The metal compound may be a phosphate or arsenate and so provide the oxyacid of phosphorus or arsenic, in which case an additional acid may be required, e.g. hydrochloric or nitric acid.

A wide range of metal compounds may be used. Simple inorganic salts including oxides and hydroxides are suitable, such as halides, carbonate, nitrate, phosphate, perchlorate and cyanate. Sulphates may be used in some applications but they can be disadvantageous for some purposes owing to the difficulty with which they are thermally decomposed.

Also suitable are salts of organic acids such as acetates, benzoates, oxalates, propionates or formates. Alkoxides are also useful.

Alternatively co-ordination complexes of the metal may be used, for example complexes having ligands derived from acetylacetone, ethylenedithiol, ethanolamine, carbon monoxide or phosphines.

Mixtures of metal salts and ligand-forming reagents may be used. Also, two or more salts or complexes of the same or different metals may be used, if desired.

The preparation of compositions containing a wide range of metals will be described in detail later.

The solvent is selected from the wide range of organic solvents which dissolve the components of the composition. Aliphatic alcohols containing 1 to 10 carbon atoms are particularly convenient, especially lower molecular weight alcohols containing 1 to 4 carbon atoms, for example methanol, ethanol, n- or isopropanol and substituted alcohols especially methoxy- or ethoxy-ethanol. Suitable esters are ethyl acetate or carbonate. Acetyl acetone may be used. Tetrahydrofuran is the most preferred ether to use, though dioxan may also be used. Aromatic hydroxy compounds can be used, but solubility is low in such materials.

The reactants used may be brought together in any desired order, but we prefer to add the oxyacid or a precursor thereof to the metal compound dissolved or suspended in the organic solvent.

We prefer to prepare compositions in which the metal and oxyacid are present with atomic ratios of metal to phosphorus or arsenic from 1:0.1 to 1:2.9 more preferably 1:0.5 to 1:2.

The composition may be prepared over a wide range of temperatures, for example from 50°C to 150°C, but generally we prefer to mix the components at temperatures below about 60°C. The process may, if desired, be carried out at pressures above normal atmospheric pressure, but it is found that, generally, if the temperature is kept below the normal boiling point of the solvent, such excess pressure is not needed.

For optimum product yield and purity all the steps in the preparation including any preparatory operations are preferably carried out under conditions in which little additional water is introduced apart from that provided by the components such as water of crystallisation from metal compounds or water from phosphoric acid. It is not essential, however, to maintain anhydrous conditions; in fact up to about 25% by weight of the composition may be water, though the precise upper limit depends on the choice of solvent and metal concentrations and is best determined by small scale trial.

Additional components such as pigments, polymers, colourants, surfactants or sources of other ions and other additives may be included in the compositions, but since the purpose of the additional component is related generally to uses of the composition, detailed discussion will be deferred until a later section.

The liquid compositions may be converted into dry compositions by removal of the solvents, provided the compositions are maintained in an atmosphere of the solvent. Spray-drying is a convenient technique for producing solids. These may be redissolved in suitable solvents of the type described to reconstitute the liquid composition.

The solubility of our compositions in organic solvents is due to complex formation. These complexes may be isolated and their nature and typical properties will now be described.

B. The Complexes

Our invention may also use metal-containing complexes in which there is associated with a metal ion one or more phosphate or arsenate ligands and one or more organic ligands, the organic ligands being derived from organic compounds containing an electron-donating oxygen atom or their thio-equivalents. The most commonly used organic compounds for this purpose are hydroxyl compounds, especially alcohols; carbonyl compounds including aldehydes, ketones and esters; nitro compounds and ethers including cyclic ethers. Of particular importance because of their ready availability are lower monohydric alcohols ROH containing 1 to 10 carbon atoms, esters of the structure $R^1COOR^2$ where $R, R^1$ and $R^2$ are alkyl groups or substituted alkyl groups containing from 1 to 10 carbon atoms each, ethers or ketones of the structure $R^1—O—R^2$ or $R^1—CO—R^2$ nitro compounds of the formula $R^1NO_2$, where $R^1$ and $R^2$ have the meaning ascribed above, and ethers of the structure $OR^3$ where $R^3$ is a divalent alkyl group having up to 7 carbon atoms one of which may be replaced by a oxygen atom.

The complexes are difficult to characterise structurally because some of the liquids are rather labile but the evidence which will be discussed indicates the presence of complex ions of the structure (4) in cases where the metal has a valency of m and co-ordination number of 6 or more.

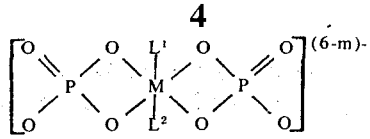

or where the co-ordination number is four, the equivalent complex ion is of the structure

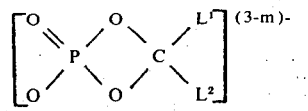

In formulae (4) and (5) $L^1$ and $L^2$ represent other ligands, at least one of which in a given ion is an organic ligand. $L^1$ and $L^2$ may be also inorganic ligands, such as halide, sulphate, nitrate or thiocyanate, when corresponding adjustment of the total valency of the ion will have to be made. Complexes may contain more than one unit of structure (4 to 5) linked together through hydrogen bonding of organic ligands $L^1$ and $L^2$: also at least one but not all of ligand pairs $L^1$ and $L^2$ may be replaced by bidentate groups such as phosphate groups. Such an ion is difficult to represent in two dimensions but a complicated structure of this type containing additional phosphate ligands accounts for the analyses of certain complexes of the invention containing trivalent metals having a metal to phosphorus ratio in the range 1:1 to 1:2.9.

Q is a metal of atomic numbr 12, 14, 20–32, 39–50, 57–80, 90 or 92, having a valency m and a co-ordination number of 4.

The counter ion associated with the anions described above may be selected from a wide range of cations but is usually hydrogen ($H^+$) or $M^{m+}$ or $Q^{m+}$.

The complexes may be characterised in several further ways. Heating the solid decomposes it to a metal phosphate and a distillate is obtained which consists mainly of an organic compound corresponding to the co-ordinated organic liquid.

Proton magnetic resonance studies on alcoholic solutions of the complexes show a shift of resonance to a field high of the usual proton resonance range and the resonance is broadened. For example an iron complex in methanol shifts the resonance 30 ppm high. That the complexes are not strongly bound together is indicated by the observation of only a single signal for solvent and ligand methanol, suggesting rapid exchange.

Infra-red or laser-Raman spectroscopy may be used to characterise the complex and to identify the presence of phosphate groups (about 900–925 $cm^{-1}$ and 1088 $cm^{-1}$) and the organic ligand. Compared with the organic compound from which the ligand is derived the peaks in the spectrum of the complex often show a shift (in one or other direction) of 3–12 $cm^{-1}$, suggesting weak coupling.

Ultra-violet spectroscopy may be used to characterise the environment of the metal, conveniently by evaporating a solution of the complex on a quartz plate and measuring ultra-violet transmission over the range 200 to 450 millimicrons. In the examples at the end of this specification ultra-violet characteristics of complexes of a number of metals will be described in detail.

C. Methods of Preparing Complexes

Several methods will be described, all of which have in common the feature of bringing together, in a solvent for at least one component or the product complex, a source of an oxyacid of phosphorus or arsenic, a source of metal ions and a source of organic ligands. Conveniently the source of organic ligands is the solvent or part of the solvent. The differences between the several processes described are mainly in connection with the method of isolating the product complex from the compositon. For any given solvent or mixture of solvents, the process conditions can be adjusted either to maintain the complex in solution, or to precipitate it, according to whether its solubility product is exceeded. Precipitation can be achieved, for example, by selection of the solvent, by concentration, by altering the temperature and/or pressure, or by addition of a further component in which the complex has a low solubility. For some purposes however such isolation is not necessary, for the compositions may be used as prepared. Since the organic ligands are usually rather labile, if the isolated complex is to be stored, it should be maintained in an atmosphere of the ligand source, i.e. the organic solvent which provides the ligand.

According to a first process for preparing a complex for use in our invention, an oxyacid of phosphorus or arsenic or a source thereof, a metal compound and a source of organic ligands are brought together in an organic medium which is capable of dissolving the components, but in which the solubility product of the resulting complex is exceeded. The complex phosphate or arsenate produced may be isolated for example by filtration, decanting off the remaining liquid or by centrifuging. The product may be dissolved in another solvent, e.g. an alcohol, for use.

Suitable organic media for this process include ethers, preferably cyclic ethers, esters, alcohols, ketones, nitro-compounds, amides, carbonates, sulphones, sulphoxides and mixtures of such solvents. Examples of such suitable solvents are tetrahydrofuran, dimethyl sulphoxide, ethylene carbonate, propylene carbonate, acetone, methyl ethyl ketone, methyl acetate, n-propyl alcohol, n-butyl alcohol, ethyl acetate, nitromethane, ethyl acrylate and diethyl carbonate.

The reactants used may be brought together in any desired order, but we prefer to add the oxyacid, or a precursor thereof, to the metal compound dissolved in the organic medium.

In this case the oxyacid, or precursor thereof is added directly or in solution to a solution of the metal compound, to precipitate the complex.

According to a second process for preparing a complex for use in our invention, a metal compound, a source of organic ligands and the oxyacid of phosphorus or arsenic or precursor thereof, are dissolved in a solvent for the components and the reaction product, then the complex is separated by adding a phase separator to the reaction mixture.

The phase separator is an organic substance which is miscible with the solvent used but in the presence of which the solubility product of the complex is exceeded. Thus the complex separates out as a solid or as an oil.

The phase separator is preferably a substance having a low dielectric constant, especially a dielectric constant from 2 to 11. Most preferred phase separators have a low co-ordinating power for the metals of the compounds used in the process. It is usual for the phase separator to be a liquid at the temperature at which the process is carried out; preferred liquids are hydrocarbons and halogenated derivatives, for example methylene chloride, trichloroethylene, carbon tetrachloride, chloroform, ethylene dichloride, methyl chloroform, chlorobenzene, toluene, xylene, benzene or $C_6$ to $C_{12}$ aliphatic hydrocarbons. Certain organic liquids can act as co-ordinating ligands or as phase separators. For example, in the presence of methanol as principal solvent and organic ligand source, diethyl ether may act as a phase separator. In the absence of a solvent of such high co-ordinating power as methanol, diethyl ether may act as a co-ordinating solvent. Best results therefore require a certain amount of straightforward trial. Some degree of concentration of the solution may be required e.g. evaporation under low pressure, before the phase separator is added.

Reaction conditions of temperature, pressure and metal to phosphorus ratio are generally as described above in connection with the compositions.

D. Properties of Compositions, Complexes and their Solutions

A particular property of these materials which makes them useful for many technical purposes is their ability to decompose to mainly amorphous metal phosphates which are highly insoluble in solvents for the original composition. In essence the composition is heated to remove any solvent which remains and also the co-ordinate organic ligands which are responsible for conferring solubility on the complex. Further heating may be advantageous in removing bound water to give greater insolubility.

When a complex has been isolated, it is preferably dissolved as prepared, or in at least partly purified form, in a suitable solvent before decompositon. A suitable solvent may conveniently be selected from the organic co-ordinating solvents used in the preparation of a composition or complex. Some water may be present, provided the complex remains in solution.

Useful protic solvents are for example, methanol, ethanol, cyclohexanol, n-propanol, benzyl alcohol and especially methanol. Higher alcohols, substituted alcohols, polyfunctional alcohols and aromatic alcohols, for example butanol, 2-methoxy-ethanol, 2-ethoxy-ethanol, 2-butoxy-ethanol, trichloroethanol, trifluoro-ethanol, bromomethanol, ethylene glycol, glycerol and cresol may also be used as solvents. Aprotic solvents may also be used, for example tetrahydrofuran, N,N-dimethyl formamide, N-methyl pyrrolidone, N,N-dimethyl acetamide, dimethyl sulphoxide, ethylene carbonate, propylene carbonate, acetone, methyl ethyl ketone, ethyl acetate, methyl acetate and nitromethane. Especially useful solvent mixtures are derived from methanol or ethanol and a chlorinated hydrocarbon, for example, chloroform, methylene chloride, ethylene dichloride and trichloroethylene; from methanol and methyl ethyl ketone or tetrahydrofuran; from methanol and dimethyl formamide; from methanol and chloral hydrate and from methoxy- or ethoxy-ethanol and toluene.

Decompositon of the composition is preferably carried out by heating or by air-drying at room temperature, optionally under reduced pressure.

Heating may be carried out at comparatively low temperatures, for example from 30° to 120°C, to form the phosphate or arsenate of the metal. Stronger heating, for example at temperatures greater than 150°C up to 1000°C, can produce a phosphate or arsenate of the metal of somewhat different composition, due it is believed, to condensation and cross-lining. The duration of heating varies over a wide range depending upon the particular compositon and the desired end-product and is typically from practically instantaneous, as when a solution is sprayed onto a hot surface, up to 100 hours.

E. Uses of Compositions and Complexes in Forming Coatings

A composition, including a complex or a solution of a complex of the type described, may be used to coat organic polymer substrates by applying it to the substrate and subsequently allowing it or causing it to decompose to form an insoluble coating of the phosphate or arsenate of the metal, the coating being in the range 0.01 to 5 microns thick. The substrate may take up a variety of shapes, e.g. fibre, filament, sheet, granule, powder or cenospheres. The substrate may be coated with or impregnated with solution. The coatings are usually non-crystalline. A complex metal phosphate for use in the invention can be used to produce heat-stable, inert, transparent, hard films of a phosphate of a metal, especially films of the phosphates of iron, titanium, vanadium or chromium. Coatings of phosphate may be prepared in relatively thick layers for each application of coating solution. Ferric phosphate and titanium phosphate and mixtures of the two have useful ultraviolet radiation absorbing properties; chromium phosphate is useful when coated on polymers to enhance the water and alkali-resistance of the glass. We have found that coatings of thickness in the range 0.01 to 3 microns, preferably 0.2 to 2.5 microns give the best results. Thick coatings may be produced by repeated coatings, with or without conversion to phosphate between each stage. Mixtures of two or more metals may be present in the compositions. Aluminium compounds may also be present.

A convenient method for applying the coating comprises dip-coating, spraying, powder-, roller- or brush-coating the substrate to be coated with a compositon or solution of complex according to the invention, removing part or all of any organic solvent, then decomposing the complex to yield a phosphate, at a temperature from room temperature up to 1000°C or such lower temperature than 1000°C that is set by the maximum temperature which the substrate to be coated can withstand without damage or loss of useful properties. Of course, if at the same time as decomposing the phosphate, thermal modification of the substrate is planned, then the temperature may be set accordingly.

The coating solution may include additional components, for example materials which will aid the further processing of the solutions or desirably affect the properties of the coatings formed from the solutions. Thus organic materials, especially polymers or monomers, may be dissolved in the complex solution given an appropriate solvent. Examples of suitable polymers include diene polymers, acetylene polymers, vinyl and vinylidene polymers, e.g. acrylic acid and methacrylic polymers, acrylate and methacrylate polymers, polyacrylonitrile, polyethers, polysulphones, formaldehyde resins, polyesters, polycarbonates, polyamides, polyureas and polyurethanes, natural polymers and modified natural polymers and polysiloxanes. Copolymers or terpolymers of the monomers of the aforementioned may also be used. In some cases it will be convenient to dissolve the corresponding monomer in the complex solution and polymerise it later, for example simultaneously with the thermal decomposition of the complex. It will be understood that a suitable solvent or solvent mixture has to be chosen which will dissolve both the complex and the polymer.

Additional components, for example pigments, colourants, surfactants, plasticisers, antioxidants, heat stabilisers ultra-violet stabilisers, or fillers such as metal powders may also be dispersed in the composition. Additional compounds which may be introduced include materials which can control the chemical or physical nature of the solid phase of metal phosphate which is produced from the solution. Thus a boric acid ester or ether or a silicic acid ester or ether (for example methyl borate, trimethoxy boroxine or ethyl silicate) may be introduced to suppress the crystallisation of the metal phosphate.

The ultra-violet absorption properties of the coatings may be enhanced by introducing a compound of another metal. It is especially preferred to incorporate, for this purpose, a compound of chromium, iron, titanium or of a manganese which is soluble in the particular solvent used. Thus, for example manganese(II), Iron(III), or titanium(III) or (IV) or chromium(III) may be incorporated in the solution from which the coating is formed.

The ultra-violet absorption properties of the coating may also be enhanced by introduction of organic compounds which themselves absorb in the ultra-violet, for example benzophenones and benzotriazoles. When the solubility of the organic compound allows, it may be dissolved in the solution from which the coating is formed; alternatively the organic compound may be introduced in particulate form by slurrying with the solution of the complex. If desired, both transition metals and organic compounds may be introduced into a single coating.

The chemical resistance of the coatings may similarly be enhanced by the introduction of compounds of other metals for example tin or calcium or a boron compound. Aluminium phosphate precursors may also be present.

The coatings may be used to modify the surface energy of the substrate to give hydrophilic or hydrophobic coatings.

The refractive index of the coatings may be modified as desired by the incorporation of metal compounds or organic polymers.

In certain applications particulate solids may usefully be dispersed in the solutions of the complex as for example, refractory materials such as silica, or metal oxides including titania and zirconia may be so dispersed to produce, on decomposition of the complex, a metal phosphate coating containing refractory materials. Thus the inclusion of graphite is useful in producing an electrically-conducting metal phosphate. Solid-phase lubricants such as graphite, molybdenum sulphide, poly(carbon monofluoride) and polytetrafluoroethylene, may be present.

Metal phosphate coatings may advantageously be employed as coatings for a wide variety of natural and synthetic organic polymeric substrates. Natural polymers which may be coated include cellulosic polymers and materials derived therefrom, for example wood and paper. Synthetic polymers which may be coated include polyolefins (for example polymers and copolymers of ethylene, polypropylene, butadiene, isoprene, 4-methyl pentene-1 and styrene), copolymers of ethylene with unsaturated esters (for example with vinyl acetate or alkyl acrylates or methacrylates), modified polystyrene copolymers (for example a styrene-maleic anhydride and styrene-acrylonitrile copolymer), polymers and copolymers of other ethylenically-unsaturated monomers (for example vinyl chloride, vinylidene chloride, chloroprene, methyl methacrylate, ethyl acrylate and vinyl acetate), polyphenylene oxides and sulphides, polysulphones, polyoxymethylenes, polyamides, (for example polycaprolactam (nylon 6), polyhexamethylene adipamide (nylon 6-6) and polyundecanolactam (nylon 11), and polycarbonates and polyesters (for example polyethylene 1,2-diphenoxyethane-4,4'-dicarboxylate and polyethylene terephthalate).

A coating of the phosphate complex may be applied to the polymeric substrate by a variety of techniques, for example by dipping, spraying or by roller-, brush- or powder-coating. The coating may be deposited in a single coating operation or in a succession of such operations, depending upon the thickness desired, the concentration and composition of the solution of the complex employed, and the conditions employed in the deposition of the initial coating and in its subsequent decomposition to yield the phosphate. It will be understood that the permissible temperature of decomposition will depend upon the particular substrate to be coated, and the susceptibility of the substrate to deformation or degradation will be very important in guiding the choice of decomposition conditions.

In utilising the ultra-violet absorption characteristics of the coatings of iron phosphate on polymeric materials it is preferred to use a coating at least 0.4 micron in thickness since the use of thinner coatings (for example coatings less than 0.2 micron in thickness) may accelerate the photodegradation of the polymeric substrate. The acceleration of the photodegradation may in fact, find useful practical application in the coating of certain plastics materials, especially materials used in packaging (e.g. plastics films or containers) when it is desired to overcome the problems posed by disposal of non-degradable waste materials, especially polypropylene and polyvinyl chloride. The mechanism of the acceleration of photodegradation is not fully understood but as the thickness of the coating is increased this effect appears to be overwhelmed by the effect of increased ultra-violet absorption by the thicker coating. Whichever effect is desired in a particular application, the optimum thickness will depend, for example, upon the particular polymeric substrate and upon the effect of any other components which may be incorporated in the iron phosphate coating.

For use in applications where anti-static properties are desirable considerations similar to those described for glass substrates apply.

Polymeric substrates coated with phosphate coatings find application in a wide variety of contexts and the substrates may take various forms, for example sheets, tapes and other shaped articles.

The phosphate or arsenate coating may form a primer or anchor coating for the surface of paper or plastics material which is to be painted, printed or metallised, or further coated with one or more phosphate or arsenate coatings.

The gas and water impermeability of the phosphate coatings is especially advantageous in the coating of plastics materials, for example films or containers, for use in packaging of foodstuffs. The abrasion resistance of the coatings may be utilised, for example, in the coating of plastics tapes (for example polyester tapes) and rigid sheets such as polymethylacrylate and polystyrene.

The ultra-violet absorption characteristics of iron phosphate coatings may be utilised in applications where rigid plastics sheets or formed bodies are intended for use under conditions of intense illumination, for example in light-shades especially light-diffusers for use in conjunction with fluorescent tubes. The coatings may also be used to reduce ultra-violet degradation of wood, for outdoor use.

The invention is illustrated but not limited by the following Examples:

EXAMPLE 1

A filtered solution of anhydrous ferric chloride (350 g) in "Analar" grade methanol (255 ml) was treated at room temperature with 131 ml of 88% orthophosphoric acid. The mixture was then stripped of excess methanol by means of a rotary evaporator, and the residual liquor stripped further under dynamic vacuum. The distillate from this stripping contained a large quantity of hydrogen chloride. The syrupy concentrate was then treated at room temperature with three times its volume of methylene chloride and shaken vigorously. The white solid complex derivative obtained at this stage was filtered off and washed free of soluble iron (as $HFeCl_4$) with methylene chloride. The residual solid was dissolved in methanol to give a viscous solution (Solution A) containing, by weight, 12.0% Fe and 14.0% P corresponding to an atomic ratio Fe/P = 1/2.1.

A portion of Solution A was diluted with methanol to give a solution containing, by weight, 4.1% Fe (Solution B).

A sample of polyester sheet ("Melinex" polyethylene terephthalate) 6 cm square and 25 microns thick was coated with the complex iron phosphate derivative by dipping in a portion of Solution B, the sheet being withdrawn from the solution at the rate of nine inches per minute. This coating was dried in a stream of nitrogen at ambient temperature for 15 minutes and then "cured" by heating at 120°C for 30 minutes to yield the final coating of an iron phosphate. The thickness of the iron phosphate coating on each side of the polyester sheet was 0.4 micron.

The permeability of the coated sheet was measured at 27°C and 76.9 cm Hg after degassing for twelve hours under reduced pressure. The total permeability of the coated polyester sheet was found to be $2.3 \times 10^{-20}$ mole meter Newton$^{-1}$ sec$^{-1}$, corresponding to the value of $6.1 \times 10^{-22}$ mole meter Newton$^{-1}$ sec$^{-1}$ for the permeability of the iron phosphate coating.

By way of comparison the total permeability of an uncoated sample of the same polyester sheet measured under the same conditions was $3.1 \times 10^{-18}$ mole meter Newton$^{-1}$ sec$^{-1}$.

EXAMPLE 2

A portion of Solution A (as described in Example 1) was diluted with methanol to give a solution containing, by weight, of 6.0% Fe (Solution C).

Solution C was used to coat a sample of polyester sheet ("Melinex" polyethylene terephthalate) 6 cm square and 100 microns thick by the procedure described in Example 1. The coating was dried and "cured" as described in Example 1 and the thickness of the iron phosphate coating on each side of the polyester sheet was 1.2 micron.

11

The total permeability of the coated polyester sheet was found to be $4.3 \times 10^{-19}$ mole meter Newton$^{-1}$ sec$^{-1}$, corresponding to the value of $9 \times 10^{-21}$ mole meter Newton$^{-1}$ sec$^{-1}$. for the permeability of the iron phosphate coating.

EXAMPLE 3

A portion of Solution A (as described in Example 1) was diluted with methanol to give a solution containing, by weight, 2.0% Fe (Solution D).

Solution D was used to coat a sample of polypropylene sheet 6 cm square and 24 microns thick by the procedure described in Example 1. The coating was dried and "cured" as described in Example 1 except that the "curing" was carried out at a temperature of 90°C for 150 minutes. The thickness of the iron phosphate coating on each side of the polypropylene sheet was 0.15 micron.

The total permeability of the coated polypropylene sheet was found to be $2.4 \times 10^{-18}$ mole meter Newton$^{-1}$ sec$^{-1}$, corresponding to the value of $3 \times 10^{-20}$ mole meter Newton$^{-1}$ sec$^{-1}$ for the permeability of the iron phosphate coating.

EXAMPLE 4

Another sample of polypropylene sheet (as described in Example 3) was coated using the procedure described in Example 3 except that a second layer of the coating was applied by repetition of the coating, drying and "curing" process. The thickness of the iron phosphate coating on each side of the polypropylene sheet was 0.3 micron.

The total permeability of the coated polypropylene sheet was $9.3 \times 10^{-19}$ mole meter Newton$^{-1}$ sec$^{-1}$, corresponding to the value of $6.2 \times 10^{-21}$ mole meter Newton$^{-1}$ sec$^{-1}$ for the permeability of the iron phosphate coating.

EXAMPLE 5

Solution B (as described in Example 1) was used to coat strips of "Darvic" rigid polyvinyl chloride sheet 4½ inches long and 1 inch wide by the procedure described in Example 1 except that only one-half of the area of each strip was coated. The thickness of the iron phosphate coating on each side of the coated portion of each strip was 0.4 micron.

The strips were then subjected to the radiation from a "Hanovia" U.V. 500 mercury arc lamp, the strips being placed at a distance of about eight inches from the lamp. After exposure of the radiation for five hours, the coated portions of the strips had acquired a very slight brown colouration whereas the uncoated portions had become darker brown and chalky in appearance.

EXAMPLE 6

4.6 g of manganous chloride hydrate ($MnCl_2.2H_2O$) were added to 100 g of Solution B (as described in Example 1) to give Solution E.

Solution E was used to coat strips of "Darvic" rigid polyvinyl chloride sheet by the procedure described in Example 1, except that only one-half of the area of each strip was coated and that "curing" was carried out at 70°C for 30 minutes. The process of coating, drying and "curing" was repeated and the thickness of the final coating on each side of the coated portion of each strip was 0.8 micron.

12

The strips were subjected to the radiation from a mercury arc lamp as described in Example 5. After exposure to the radiation for five hours, the coated portions of the strips had retained their positive colourless appearance whereas the uncoated portions had become brown and chalky in appearance.

EXAMPLE 7

A portion of Solution A (as described in Example 1) was diluted with methanol to give a solution containing, by weight, 1.0% Fe (Solution F).

Solution F was used to coat strips of "Darvic" polyvinyl chloride sheet by the procedure described in Example 5. The thickness of the iron phosphate coating on each side of the coated portion of each strip was 0.1 micron. The strips were subjected to the radiation from a mercury arc lamp as described in Example 5. After exposure to the radiation for three hours the coated portions had become very dark brown relative to the uncoated portions, thus illustrating the effect of acceleration of photodegradation brought about by thin coatings of the iron phosphate.

EXAMPLE 8

A portion of Solution A (as described in Example 1) was diluted with methanol to give a solution containing, by weight, 1% Fe (Solution G).

A sample of polyester sheet ("Melinex" polyethylene terephthalate) 6 cm square and 25 microns thick was coated with the complex iron phosphate derivative using Solution G by the procedure described in Example 1. The "curing" of the coating was carried out at 100°C for three minutes. The thickness of the iron phosphate coating on each side of the polyester sheet was 0.07 micron.

The surface resistivity of the coated sheet was measured at 60% relative humidity, using a "Ultra Megometer" instrument, and was found to be $1.4 \times 10^8$ ohms/cm$^2$. By way of comparison, the surface resistivity of the uncoated polyester sheet was more than $10^{16}$ ohms/cm$^2$.

Further samples of the same polyester sheet were coated by the same process, using methanol solutions containing different concentrations of the complex iron phosphate derivative, giving rise to coatings of different thicknesses. The surface resistivity was measured, as follows:

| Solution | % Fe by weight | Thickness of coating (microns) | Surface resistivity ohms/cm$^2$ |
| --- | --- | --- | --- |
| H | 1.5 | 0.10 | $9.5 \times 10^7$ |
| I | 2.5 | 0.17 | $4.9 \times 10^7$ |
| J | 5.0 | 0.45 | $1.2 \times 10^7$ |

What we claim is:-

1. A method of applying a continuous coating consisting essentially of a metal phosphate to the surface of an organic polymer article comprising applying to the surface a liquid composition containing a solution of
   a. a compound of a metal selected from the group consisting of Mg, Ca, Sc, Ti, V, Cr, Mn, Fe, Co, Ni, Cu, Zn, Ga, Ge, Y, Zr, Nb, Mo, Tc, Ru, Rh, Pd, Ag, Cd, In, Sn, Ba, La, Ce, Pr, Nd, Pm, Sm, Eu, Gd, Tb, Dy, Ho, Er, Tm, Yb, Lu, Hf, Ta, W, Re, Os, Ir, Pb, Au, Hg, Th and U; and b. an oxyacid of phosphorus or a compound capable of forming such an oxyacid in the solution, the oxyacid being an ortho- or meta-acid of the structure (1)

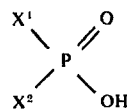

Where $X^1$ and $X^2$ are the same or different and selected from hydrogen, hydroxyl, halide or which have the structure (2) to provide pyrophosphoric acid

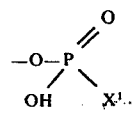

wherein the solvent is a solvent for both components (a) and (b) and contains an organic component and the atomic ratio of metal to phosphorus is in the range 1:0.1 to 1:2.9 and converting the coating so formed to a metal phosphate by air-drying or by heating to give a coating of 0.01 to 5 microns thickness.

2. A method as claimed in claim 1 in which the composition is applied by dip-coating, spraying, or by roller- or brush-coating.

3. A method as claimed in claim 1 in which the metal compound comprises an iron compound and the oxyacid of phosphorus is orthophosphoric acid.

4. A method as claimed in claim 1 in which the metal compound comprises a mixture of an iron and titanium compound.

5. A method as claimed in claim 3 in which the organic polymer is in the form of a sheet or film.

6. A method as claimed in claim 3 in which the organic polymer is a polyester.

7. A method as claimed in claim 6 in which the polyester is poly(ethylene terephthalate).

8. A method as claimed in claim 3 in which the organic polymer is polypropylene.

9. A method as claimed in claim 1 in which the coating applied to the organic polymer is heated at a temperature of 30°C. to 120°C. to form the metal phosphate.

* * * * *